United States Patent [19]

Tsaknis et al.

[11] 4,158,709

[45] Jun. 19, 1979

[54] METHOD FOR COLLECTING HISTOLOGIC MATERIAL

[75] Inventors: Peter J. Tsaknis, Mt. Airy, Md.; Virginia J. Lux, Dover, Del.

[73] Assignee: The United States of America as represented by the Secretary of the Army, Washington, D.C.

[21] Appl. No.: 900,389

[22] Filed: Apr. 26, 1978

[51] Int. Cl.² ............................................. G01N 31/00
[52] U.S. Cl. ...................................... 427/2; 248/127; 424/3
[58] Field of Search ........................ 248/127; 356/244; 427/2; 424/3

[56] References Cited

U.S. PATENT DOCUMENTS

| 386,689 | 7/1888 | Clark | 248/137 |
|---|---|---|---|
| 1,647,565 | 11/1927 | Furlong | 248/137 |

Primary Examiner—Sam Silverberg
Attorney, Agent, or Firm—William G. Gapcynski; Werten F. W. Bellamy; Sherman D. Winters

[57] ABSTRACT

An apparatus and method for the recovery of small plastic tissue sections is described. A container having parallel sides is rotatably supported on its ends. Slides are placed in the container at an angle. The container is filled with a liquid and the histologic specimens are floated on the liquid within the receptacle. The container is then tilted so that the slides are horizontal and the sections are floating over the slides. A valve allows release of the liquid from the container into a trough. When the water level falls just below the level of the slides the valve is closed and the slides are removed from further processing.

1 Claim, 2 Drawing Figures

METHOD FOR COLLECTING HISTOLOGIC MATERIAL

BACKGROUND OF INVENTION

1. Field of the Invention

The invention generally relates to an apparatus for the collection of histologic material by floatation and, specifically, relates to the use of a rotatably mounted container to collect tissue specimens on slides.

2. Description of the Prior Art

Collection of histologic material in the prior art is accomplished by recovery of the tissue specimens through dipping of a slide in a container of water where the floating sections of tissue were placed and manually picking up the sections by lifting the slide. Because of the size of the tissue sections, which are often comparable to the point of a pencil, the movement of the water caused by the slide coming up under the section for recovery causes the section to move away from the slide. The technician must employ both speed and agility to recover even a few specimens. The traumatic effect on the tissue section and the stress placed on the technician often cause folds and tears in the tissue. These folds trap stain within the tissue as well as chemicals which could adversely affect the final tissue stain. This also results in many sections falling off the slides during the staining procedure. The folded sections that remain on the slide result in research projects being significantly affected or, in the case of a surgical pathologic specimen, the quantity sufficiently affected to place the diagnosis by the pathologist in jeopardy.

SUMMARY OF THE INVENTION

A container having parallel sides is rotatably mounted by supporting the ends of the container in vertical supports which are connected to the sides by pins perpendicular to the sides. A valve is located in the container to allow release of liquids in the container. The inner portion of one side of the container has a ridge thereon for supporting one end of the slide. The other side of the container has a top edge which is tapered to support the other end of the slide. The slide is placed in the container at an angle supported by the ridge and by the tapered edge. The container is filled with water and the histologic material to be collected is floated on the surface of the water. The container is then rotated until the slides are horizontal. The valve is then opened to release the water in the container into a trough. As the water level decreases in the container, the specimens to be collected rest upon the base of the slide. When the water level is below the slides, the slides are removed for further processing.

It is an object of this invention to provide a floatation receptacle for the collection of histologic specimens which eliminates the task of the technician chasing and picking up the tissue sections.

It is the further object of this invention to provide a receptacle for collecting histologic material which allows quick placement of the specimens on the slides.

It is yet another object of this invention to provide a receptacle for collecting histologic material which eliminates the problem of causing folds and tears in the specimens to be collected.

BRIEF DESCRIPTION OF THE DRAWINGS

These and other objects will become apparent to those skilled in the art by referring to the following figures wherein.

DETAILED DESCRIPTION OF THE INVENTION

Container 1 has parallel sides 2 and 3 which are connected to ends 4 and 5 and bottom 6. Stop valve 7 is located in the container to allow release of any liquids which are in the container. Trough 8 is located below the stop cock valve 7 for the collection of any liquids which are released.

Figure 2:
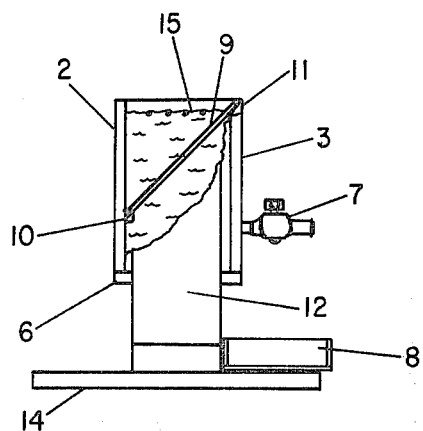
FIG. 2 is a side view of the receptacle with portions cut away showing the initial placement of the slide before rotation of the receptacle.

As shown in FIG. 2, slides 9 are placed in the container while the container is in the upright position. The slides 9 are angularly supported by ridge 10 and by tapered edge 11 of side 3. The container is filled with any convenient liquid such as water and the histologic specimens 15 to be collected are floated on the surface of the liquid.

The container is supported by vertical supports 12 and 13 which are connected to base 14. The container 1 is rotatably supported by pins (not shown) which are perpendicularly attached to sides 4 and 5 and supported in groves 17 located in vertical supports 12 and 13. Handle 16 is attached to the pins to allow rotation of the container.

Figure 1:
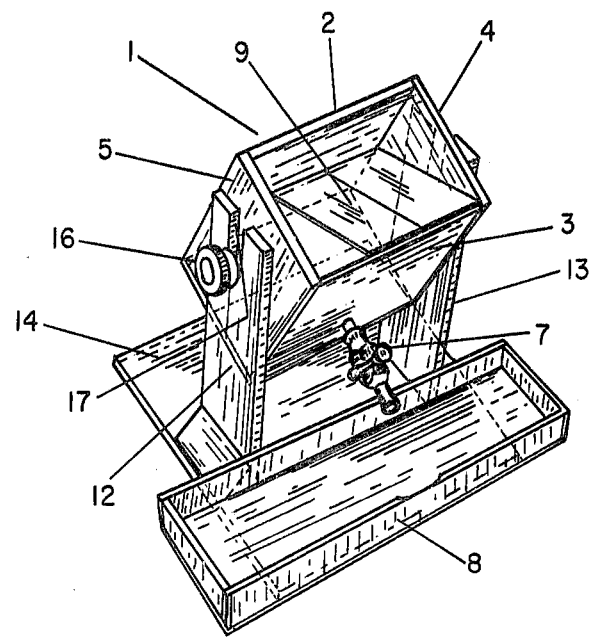
FIG. 1 is an perspective view of the collection receptacle in a rotated position.

To collect the specimens, the container is rotated until the slides are in a horizontal position as shown in FIG. 1. The valves 7 are then opened to release the liquid from the container. The floating specimens 15 rest upon the slides 9 as the water level falls below the level of the horizontal slides 9. The slides are then removed for further processing.

The method of collection of the histologic material includes the steps of placing slides in a liquid and supporting the slides diagonally within the liquid. Specimens to be collected are floated on the surface of the liquid. The container in which the liquid is held is then rotated to a position where the slides are horizontal. The liquid is then removed from the container allowing the floating specimens to rest upon the slides.

I claim:

1. A method for depositing histologic material on a slide located in a container which contains a liquid comprising the steps of:
   a. placing the slide in the liquid;
   b. supporting the slide diagonally;
   c. floating the histologic material on the liquid;
   d. rotating the container to a position where the slide is horizontal and the histologic material is floating over the slide; and
   e. removing the liquid from the container thereby allowing said floating histologic material to settle upon the slide.

* * * * *